United States Patent [19]

Mintz

[11] Patent Number: 5,208,357
[45] Date of Patent: May 4, 1993

[54] CHIRAL METALLOCENE COMPOUNDS AND PREPARATION THEREOF BY ATTACHMENT OF CHIRAL CENTER

[75] Inventor: Eric A. Mintz, Doraville, Ga.

[73] Assignee: Exxon Chemical Patents, Inc., Linden, N.J.

[21] Appl. No.: 636,403

[22] Filed: Dec. 31, 1990

[51] Int. Cl.$^5$ .................. C07F 9/00; C07F 17/00; C07F 13/00; C07F 11/00

[52] U.S. Cl. ...................... 556/43; 556/47; 556/53; 556/60; 556/143; 556/465; 556/489; 568/8; 568/59; 568/666; 568/667; 568/671; 585/350; 585/375

[58] Field of Search .............. 585/350, 375; 556/43, 556/47, 53, 60, 143, 489, 465; 568/59, 8, 666, 667, 671

[56] References Cited

PUBLICATIONS

Daniel T. Mallin et al., "Synthetic, X-ray structural and polymerization studies on isopropyltetramethylcyclopentadienyl derivatives of titanium", J. Organomet. Chem., vol. 381, 1990, pp. 35–44.

Jerome C. Pando, Eric Mintz, "5-Methoxy-2,3,4,5-tetramethylcyclopent-2-enone, a Synthetic Equivalent For 2,3,4,5-Tetramethylcyclopentadienone: Application to the Synthesis of 1,2,3,4-Tetramethylfulvene", Tetrahedron Letters, vol. 30, No. 36, 1989, pp. 4811–1812.

Gerhard Erker et al., "Double Stereodifferentiation in the Formation of Isotactic Polypropylene at Chiral $(C_5H_4CHMePh)_2ZrCl_2$/Methylalumoxane Catalysts", Angew. Chem. Int. Engl. 28, 1989 No. 5, pp. 628–629.

Dennis M. Bensley, Jr. and Eric A. Mintz, "1,2,3,4,6-Pentamethylfulvene: a convenient precursor to substituted tetramethylcyclopentadienyl transition metal complexes" J. Organomet. Chem., vol. 353, 1988, pp. 93–103.

Dennis M. Bensely, Jr. et al. "Synthesis of $[C_5(CH_3)_4H]CH_2CH_2CH_2P(C_6H_5)_2$: A Novel Heterodifunctional Ligand Possessing Both a Tetramethylcyclopentadiene and a Remote Diphenylphosphine Functionality". J. Org. Chem., vol. 53, 1988, p. 4417.

Ronald L. Halterman and K. Peter C. Hollhardt, "Synthesis and Asymmetric Reactivity of Enantiomerically Pure Cyclopentadienyl metal Complexes Derived from the Chiral Pool", Organometallics, 1988, vol. 7, pp. 883–892.

Emilio E. Bunel et al., "Synthesis of p-Phenylene- and p-Biphenylene-Bridged Methylated Bionuclear Ferrocenes" Organometallics, vol. 7, No. 2, 1988, pp. 474–476.

George W. Parshall, William A. Nugent, "Making pharmaceuticals via homogeneous catalysis", Chemtech, Mar. 1988, pp. 184–190.

George W. Parshall and William A. Nugent. "Functional chemicals via homogeneous catalysts", Chemtech, May 1988, pp. 314–320.

George W. Parshall, William A. Nugent, "Homogeneous catalysis for agrochemicals, flavors, and fragrances", Chemtech, Jun. 1988, pp. 376–383.

Paavo O. Lumme and Urho Turpeinen, "Crystal and molecular structure of [3-($^5$n-tetramethylcyclopentadienyl)-1-($n^6$-meisityl)propane]ieridium(II) bistetrafluoroborate mononitromethane", J. Organomet. Chem, vol. 348, 1988, pp. 255–260.

(List continued on next page.)

Primary Examiner—Jose G. Dees
Assistant Examiner—Porfirio Nazario-Gonzalez
Attorney, Agent, or Firm—Myron B. Kurtzman; M. Susan Spiering; D. W. Miller

[57] ABSTRACT

There are provided enantiomerically enhanced chiral substituted cyclopentadienyl ligands and compounds thereof, and a process for their making comprising contacting a substituted fulvene or derivative thereof with an enantiomerically enhanced or pure nucleophile having at least one chiral center. There are further provided enantiomerically enhanced chiral organometallic complexes having one or more chiral substituted cyclopentadienyl groups.

35 Claims, No Drawings

PUBLICATIONS

Gallucci, et al. "Bis(isodicyclopentadienyl) Complexes of the Group 4 Transition Metals. Stereoselective Synthesis and Crystal Structures of the Titanocene and Zirconocene Dichloride Derivatives" *Organometallica*, vol. 6, 1987, pp. 15–19.

J. F. Buzinkai and R. R. Schrock, "Heterobimetallic Complexes Connected by Peralkylated Cyclopentadienyl Rings" *Organometallics*, vol. 6, 1987, pp. 1447–1452.

Ronald L. Halterman et al., "A designed, Enantiomerically Pure, Fused Cyclopentadienyl Ligand with $C_2$ Symmetry: Synthesis and Use in Enantioselective Titanocene-Catalyzed Hydrogenations of Alkenes", *J. Am. Chem. Soc.*, vol. 109, 1987, pp. 8105–8107.

N. E. Schore and B. E. LaBelle, "Reactions of [(Diphenylphosphino)methyl]lithium with Dimethylfulvene", *J. Org. Chem.*, vol. 46, 1987, pp. 2306–2310.

H. M. R. Heffmann and Oskar Koch, "Regioselective Preparation of Vinylcyclopentadienes and Selected Cycloaditions", *J. Org. Chem*, vol. 51, 1986, pp. 2939–2944.

Leo A. Paquette, et al., "$\pi$-Facial Stereoselectivity Operational during Conversion of Isodicylopentadienes to Metallocene Derivatives", *Organometallics*, vol. 5, 1986, pp. 490–499.

Lihong Shen and Eric. A. Minz, "Novel Reduction of 6-t Butylfulvene by Diethylaminolithium and 1,2,3,4-Tetrahydroisoquinolinyllithium", submitted to Tetrahedron Letters, Jan. 1991.

Jerome C. Pando, et al., "5-Methyoxy-and 5-Phenoxy-2,3,4,5-Tetramethylcyclopent-2-Enone as Synthetic Equivalents for 2,3,4,5-2-Enone Synthesis of 1,2,3,4-Tetramethylfulvene and 1,2,3,4,6-Pentamethylfulvene", Tetrahedron Letters, vol. 30, 1989.

H. B. Kagan, "Chiral Ligands in Asymmetric Catalysis By Transition Metal Complexes", *Annals New York Academy of Sciences*, 1980, pp. 1–15.

Jack Hine and David B. Knight, "Base-Catalyzed Deuterium Exchange of 6,6–Dimethylfulvene" *J. Org. Chem*, vol. 45, 1980, pp. 991–998.

William F. Little and Robert C, Koestler, "Preparation of Substituted Ferrocenes from Fulvenoid Compounds", vol. 26, Sep. 1961, pp. 3245–3247.

David B. Knight, et al., "Protonation and Deuteration of the Isopropenylcyclopentadienyl Anion. Trapping of the Isomeric Product Mixture", *J. Org. Chem.*, vol. 37, No. 5, 1972, pp. 688–692.

Jack Hine and David B. Knight, "Protonation of the Isopropenylcylopentadienyl Anion", *J. Org. Chem.*, vol. 35, No. 11, 1970, pp. 3946–3949.

Carol M. Fendrick, et al. *Organometallics*, vol. 3, 1984, pp. 819–812.

S. Couturier and B. Gautheron, "Synthesis and Reactions of Substituted Zirconocene and Hafnocene Dimethyls and the Corresponding Dihydrides", *J. Organomet. Chem.*, vol. 157, 1978, pp. C61–C63.

P. Renault, et al., "Chlorures De Mono-et Dialkyl–Zirconocene et–Hafnocene", *J. Organomet. Chem.*, vol. 148, 1978, pp. 35–42.

J. C. LeBlanc and C. Moise, "Complexes Derives Du Dichlorure De Titanocene A Pseudoasymetrie Centrometallee", *J. Org. Chem.*, vol. 131. 1977, pp. 35–42.

S. Couturier et al., "Synthese Et Reactivite de Nouveaux Dihydrurozirconocenes et Hafnocenes substitues Achiraux et Chiraux", *J. Organomet. Chem.*, vol. 195, 1980, pp. 291–306.

Franz Wochner, et al., "Syntheses and Crystal Structures of Ethylene-Bridged Titanocene and Zirconocene Derivatives with Permethylated Ring Ligands", *J. Organomet. Chem.*, vol. 288, 1985, pp. 69–77.

Richard S. Threlkel and John E. Bercaw, "A convenient Synthesis of alkyltetramethylcyclopentadienes and Phenyltetramethylcyclpopentadiene", *J. Organomet. Chem.*, vol. 136, 1977, pp. 1–5.

H. J. Scholz and H. Werner, "Synthese Von $Li_2[(C_5Me_4)_2CH_2]$ Und Ringverbruckter Rhodiium–Zeikernkomplexe Mit Dem $(C_5Me_4)_2CH_2$–Dianion Als Burckenliganden", *J. Organomet. Chem.*, vol. 303, 1986, pp. C-8–C12.

David Feitler and George M. Whitesides, "Convenient Preparations of 1,2,3,4,5-Pentamethylcyclopentadiene and 1-Ethyl-2,3,4,5-tetramethylcyclopentadiene", *Inorg. Chem.*, vol. 15, No. 2, 1976, pp. 466–469.

Donald J. Cram and Donalr R. Wilson, "Studies in Stereochemistry. XXXIII. Approaches to Models for 1,3–Asymmetric Induction", *J. Am. Chem. Soc.*, vol. 85, May 5, 1963, pp. 1249–1257.

Gilbert M. Brown and Norman Sutin, "A Comparison of the Rates of Electron Exchange Reactions of Ammine Complexes of Ruthenium (II) and -(III) with the Predictions of Adiabatic, Outer-Sphere Electron Transfer Models", *J. Am. Chem. Soc.*, vol. 101, No. 4, pp. 883–892 (1979).

William S. Knowled, "Asymmetric Hydrogenation", *Acc. Chem. Res.*, vol. 15, 1983, pp. 106–112.

(List continued on next page.)

PUBLICATIONS

Charles P. Casey, et al., "Synthesis of Molybdenum-Rhodium and Molybdenum-Iridium Compounds Linked by a Heterodifunctional Ligand and Formation of Molydenum-Iridium Dihydrides by Reaction with Molecular Hydrogen", *J. Am. Chem. Soc*, vol. 105, 1983, pp. 7574–7580.

M. F. Semmelhack et al., "Reduction of Coordinated Carbon Monoxide to 'Zirconoxy' Carbenes with Permethylzirconocene Dihydride", *J. Am. Chem. Soc.*, vol. 101:1, Jan. 3, 1979, pp. 218–220.

Josephine Paw Blaha and Mark S. Wrighton, "Relative Imporance of Dissociative Loss of Carbon Monoxide and Formation of Benzyl Radicals from Photoexcitation of $(n^5-C_5R_5)Fe(CO)_2(^1n-CH_2C_6H_5)$ and Evidence for Reaction of Carbon Monoxide with 17-Electron Radicals", *J. Am. Chem. Soc.*, vol. 107, 1985, pp. 2694–2702.

Donald J. Harvan, et al., "Synthesis of $(C_6H_5)_2PCH_2Si(CH_3)_2C_5H_4Li$: A Novel Heterodifunctional System for the Directed Linkage of Dissimilar Transition Metal Fragments", *J. Am. Chem. Soc.*, vol. 101:24, Nov. 21, 1979, pp. 7410–7412.

Juan M. Manriquez, et al., "Reduction of Carbon Monoxide Promoted by Alkyl and Hydride Derivatives of Permethylzirconocene", *J. Am. Chem. Soc.*, vol. 100:9, Apr. 26, 1978, pp. 2716–2724.

C. F. H. Allen and J. A. VanAllan, "Dimerization of Cyclopentadienones", J. Am. Chem. Soc., vol. 72, Nov. 1950, pp. 5165–5167.

Peter T. Wolczanski and John E. Bercaw, "On the Mechanisms of Carbon Monoxide Reduction with Zirconium Hydrides", *Acc. Chem. Res.*, vol. 13, 1980, pp. 121–127.

Prof. Dr. K. Hafner, et al., "Fulvenes as Isomers of Benzenoid Compounds", *Angew. Chem. internat. Edit.* vol. 2, 1963 No. 3, pp. 123–134.

Ernst D. Bergmann, "Fulvenes and Substituted Fulvenes", Institute for Advanced Study, Princeton, New Jersey, Apr. 12, 1967, pp. 41–75.

CHIRAL METALLOCENE COMPOUNDS AND PREPARATION THEREOF BY ATTACHMENT OF CHIRAL CENTER

BACKGROUND OF THE INVENTION

1. Field of the Invention

This invention relates to enantiomeric chiral compounds and a process for their stereoselective preparation. In another aspect this invention relates to enantiomerically enhanced or pure chiral substituted cyclopentadienyl ligands and a process for their stereoselective preparation. In yet another aspect, this invention relates to enantiomeric chiral Group III B-VIII B (the chemical Groups herein are as referenced to the Periodic Table of Elements, CRC Handbook of Chemistry and Physics, 68th ed. 1987-1988) organometallic complexes and a process for their stereoselective preparation. 2. Description of the Prior Art Stereochemistry refers to the three-dimensional spatial configurations of molecules. Stereoisomers are compounds which have identical chemical constitution, but differ as to the orientation of the atoms or groups in three dimensional space. Stereoisomers fall into one of two broad classes: optical isomers and geometric (cis-trans isomers). Enantiomers are one type of optically active three-dimensional isomers that are mirror image structures, which form as the result of the presence of one or more asymmetric or chiral centers. These mirror image forms compare to each other structurally as do the right and left hands when the chiral carbon atoms, C*, are lined up. For example, in the enantiomeric forms of glyceraldehyde, the two structures are mirror images of each other and cannot be made to coincide:

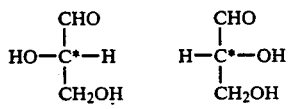

There are several conventions used when referring to respective enantionmers in a pair such as d/1, R/S, and +/−.

Pairs of stereoisomers differ so little in structure, and hence in physical properties, that they are generally differentiated by the use of a polarimeter, which measures the amount of rotation the compound imparts to polarized light as it passes through the compound. Yet despite the close similarity, one isomer of a pair may serve as a nourishing food, or as an antibiotic, or as a powerful heart stimulant, and the other isomer may be useless or even harmful. One of the most difficult problems in the preparation of compounds is the control of stereochemistry, and in particular the preparation of enantiomerically pure compounds. One of the most dramatic examples of the importance of chirality control was the use of the drug thalidomide, which was manufactured and sold as a racemic mixture (mixture of the optical isomers wherein the mixture is optically inactive). One optical isomer produced the desired therapeutic effect, while the enantiomer, which was assumed to be pharmacologically inert, led to fetal deformities.

Chiral catalytic complexes could be utilized to facilitate enantioselective transformations. For example the enantioselective hydrogenation of acetamidocinnamic acid is catalyzed by the presence of a chiral rhodium catalyst. Transition metal organometallic complexes have long been used to catalyze chemical reactions. Recently transition metal complexes incorporating chiral chelating diphosphine ligands have been successfully utilized to effect enantioselective hydrogenations. However, the stereo-differentiating ability of these complexes can suffer due to the lability of phosphine ligands.

The tremendous potential of utilizing chiral organometallic complexes to carry out enantioselective transformations is hindered by the lack of readily available enantiomerically enhanced (that is, an excess of one of the enantiomers) or pure organometallic complexes, and enantiomerically enhanced or pure ligands or compounds from which to make enantiomerically enhanced or pure organometallic complexes.

Chiral cyclopentadienes are considered to be a suitable starting point for making enantiomeric enhanced or pure organometallic complexes, however, only a small number of chiral cyclopentadienes are known and only a few of them are enantiomerically enhanced or pure. Generally, synthesis of chiral compounds from achiral reactants typically will yield the racemic modification or mixture. The enantiomers must then be separated (resolved) by special methods that are very difficult and yield less than desired results. A method that would produce an excess of the desired enanthomer could rely less on resolution techniques than a process that produced a racemic or essentially racemic mixture. There have been other attempts to develop enantiomerically enhanced or pure cyclopentadienyl ligands or compounds that have focused on preparing chiral cyclopentadienyl ligands from inexpensive naturally occurring enantiomerically enhanced or pure compounds. Unfortunately many of these routes require several synthetic steps to transform a naturally occurring starting material into a cyclopentadienyl derivative.

Therefore, the need exists in the art for an efficient, simple process for producing enantiomerically enhanced or pure cyclopentadienyl derivatives which could then be made into enantiomerically enhanced or pure organometallic compounds, without an undue amount of synthetic steps, and without having to rely entirely on resolution techniques.

SUMMARY OF THE INVENTION

According to one embodiment of this invention there are provided enantiomerically enhanced or pure chiral substituted cyclopentadienyl ligands and compounds and salts thereof.

According to another embodiment of this invention there is provided a stereoselective process of preparing enantiomerically enhanced or pure chiral substituted cyclopentadienyl ligands and compounds thereof comprising contacting a substituted fulvene or derivative thereof with an enantiomerically enhanced or derivative thereof with an enantiomerically enhanced or pure nucleophile having at least one chiral center, in a suitable solvent and under suitable reaction conditions.

According to still another embodiment of this invention there are provided enantiomerically enhanced chiral organometallic complexes having one or more chiral substituted cyclopentadienyl groups.

DETAILED DESCRIPTION OF THE INVENTION

The substituted fulvene compounds or derivatives thereof that are useful in the present invention, are of the general formula I:

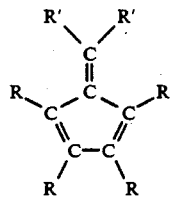

wherein each R and each R' is independently H a C₁ or higher desirably C₁-C₂ and more desirably C₁-C₈, substituted or unsubstituted, aliphatic, cyclic or heterocyclic, hydrocarbon radical, with no more than 3 R groups being H or two or more neighboring R groups are joined together to form one or more rings of 5 or more carbon atoms, preferably 5-8 carbon atoms and desirably 6 carbon atoms. Preferably, each R is independently a C₁ or higher alkyl or aromatic radical. Most preferably, each R is independently a C₁ to C₃ unsubstituted alkyl radical or two are joined to form a six numbered ring. Preferably, each R' is independently H or a C₁ or higher alkyl radical or a substituted or unsubstituted aromatic radical. Most preferably, each R' is H. Exemplary preferred compounds of general formula I include 1,2,3,4-tetramethylfulvene, 1,2,3,4-tetraethylfulyene and 1,2,3,4,6-pentamethylfulvene. Exemplary most preferred compounds of general formula I include 1,2,3,4-tetramethylfulvene and 1,2,3,4-tetraethylfulvene.

Methods of making compounds of general formula I are well known to those of skill in the art. A suitable method includes that disclosed by J. C. Pando and E. A. Mintz in Tetrahedron Letters, Vol. 30, pp. 4811-2 (1989), incorporated herein by reference. The enantiomerically enhanced or pure nucleophile suitable for use in the present invention is a chiral compound with an enantiomeric excess of either R or S isomer, capable of forming ions of general formula II:

$R^*Y^-$ (II)

wherein Y is selected from the group consisting of NR", O, S, C(R")₂, P(R"), Si(R")2; each R" is independently selected from H or C₁ or higher, substituted or unsubstituted, aliphatic, aromatic, cyclic or heterocyclic hydrocarbon radicals, or amino acid radicals; and R* contains at least one chiral carbon center and is selected from C₁ or higher, substituted or unsubstituted, aliphatic, cyclic or heterocyclic hydrocarbon radicals or amino acid radicals. Preferably R" is independently selected from alkyl and aromatic hydrocarbon radicals; and R* contains at least one chiral center and is selected from radicals of amino acids, and alkyl and aromatic hydrocarbons, and Y is NH or NR". Preferably, the nucleophile is an anion of any alpha-alkylarylamine, wherein the alkyl group has in the range of about 1 to 6 carbon atoms. Exemplary alpha-alkylarylamines suitable for this invention include alpha-methylbenzyl amine, alpha-ethylbenzyl amine, alpha-propylbenzyl amine, alpha-butylbenzyl amine, alpha-methylnaphtha amine, alpha-ethylnaptha amine, alpha-propylnaptha amine, and alpha-butylnaptha amine. Most preferably the nucleophile is the anim of alpha-methylbenzyl amine.

Generally the enantiomeric excess (excess over the racemic mixture) of the nucleophile of the present invention may be any desired enantiomeric excess of either the R or S enantiomer, even including essentially all of one enantiomer, and would depend on the desired end use of any cyclopentadienyl ligand produced from such nucleophile. Such enantiomeric excess is generally at least about 1 percent. Preferably such enantiomeric excess is at least about 5 percent, and most preferably at least about 50 percent.

The enantiomerically enhanced chiral substituted cyclopentadienyl ligands of the present invention are of the general formula III:

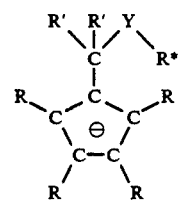

wherein R, R', R", Y and R* are as defined above.

The cyclopentadienyl ligands of the present invention can also form neutralized compounds or salts of metals such as magnesium, thallium, potassium, lithium or sodium of the following general formula IIIb or IIIc.

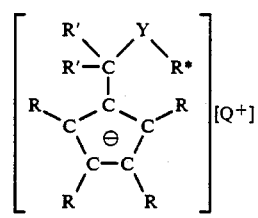

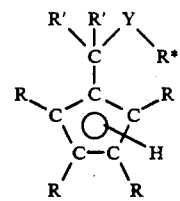

wherein R, R', R", Y and R* are as defined above, and Q is selected from the group consisting of thallium, potassium, lithium, sodium, and magnesiumhalide, wherein the halide is selected from the group consisting of chlorine, bromine, and iodine.

Generally the enantiomeric excess of the enhanced chiral substituted cyclopentadienyl ligands and compounds of the present invention may be any desired enantiomeric excess of either the R or S enantiomer, even including essentially all of one enantiomer, and would depend on the desired end use of any organometallic complex and catalyst produced from such ligands. Such enantiomeric excess is generally at least about 1 percent. Preferably such enantiomeric excess is at least about 5 percent, and most preferably at least about 50 percent.

The chiral substituted cyclopentadienyl ligands of general formula III as defined above can be made by any suitable method. One such method for preparing ligands of general formula III is by contacting a substituted fulvene compound or derivative thereof, of general formula I as described above with a nucleophile capable of forming ions of general formula II as described above, under conditions suitable to form compounds of general formula III.

Since the reaction of the substituted fulvene compound of general formula I with the chiral nucleophile, to form the enantionmerically enhanced or pure chiral substituted cyclopentadienyl ligand of general formula III, does not involve the breaking of a bond to the chiral center, the reaction will proceed with a retention of the configuration about that chiral center. This means that the degree of chirality of the resulting chiral substituted cyclopentadienyl product will be essentially the same as the chirality of the chiral nucleophile from which it was derived. Therefore to obtain a chiral substituted cyclopentadienyl product of desired enantiomeric excess or purity, the enantiomeric excess or purity of the reactant chiral nucleophile will need to be substantially the same as the desired enantiomeric excess or purity.

The substituted fulvene compounds or derivatives thereof and the nucleophile are generally contacted at a temperature that is sufficient to form the product compound of general formula III. Such temperature is generally in the range of about −78 to about 200° C. Preferably the temperature is in the range of about −50 to about 100° C. Most preferably the temperature is in the range of from about −20 to about 65° C.

The substituted fulvene compound or derivatives thereof and the nucleophile are generally contacted together at a pressure that is suitable for the formation of compounds of general formula III. Suitable pressures include those in the range of about just above 0 psia to about 2000 psig. Preferably the pressures are in the range of from about 1 psia to about 50 psig. Most preferably the pressures are in the range of from about 0 to about 16 psig.

The substituted fulvene compound or derivative thereof and the nucleophile may be contacted in the presence of any suitable solvent that will facilitate the production of compounds of general formula III. Generally the solvent is selected from the group consisting of ethers, glymes, hydrocarbons and aromatic hydrocarbons. Preferably, the solvent selected is one in which the fulvene compound is soluble. Suitable solvents include ethers such as dimethylether, diethylether and methylethylether, glymes such as monoglyme, ethyl glyme, diglyme, ethyl diglyme, triglyme, butyl diglyme and tetraglyme, tetrahydrofuran ("THF"), dimethoxyethane ("DME"), hexane, toluene and benzene.

The substituted fulvene compound or derivatives thereof and the nucleophile are generally contacted for a time sufficient to form compounds of general formula III. Suitable contacting times include those in the range of from about 0.1 minutes to about 24 hours. Preferably, the contacting time is in the range of about 0.5 hours to about 16 hours. Most preferably the contacting time is in the range of 1 to about 8 hours.

The substituted fulvene compound or derivatives thereof and the nucleophile are generally contacted together in mole ratios that are suitable for the formation of compounds of general formula III. Suitable mole ratios of substituted fulvenes or derivatives thereof to nucleophiles include those in the range of from about 10 to 1 to about 1 to 10. Preferably, the mole ratios are in the range of from about 3 to 1 to about 1 to 3. Most preferably the mole ratio are in the range of about 1.1 to 1 to about 1 to 1.1.

The metal containing compound suitable for use in the present invention is any compound having a transition metal that is capable of forming an organometallic complex with the chiral substituted cyclopentadienyl ligand of formula III. Typically the metal containing compound is a metal halide or metal carbonyl halide. Suitable transition metals include any Group III B through Group VIII B metal capable of forming an organometallic complex with the chiral substituted cyclopentadienyl ligand. Preferably, the transition metal is selected from Group IV B, VI B or VIII B, most preferably from Group IV B. Suitable metals include Ti, Hf, U, Th, Sc, V, Cr, Mn, Fe, Co and Zr. Preferably, the metal containing compound will contain a metal selected from the group consisting of Ti, Hf, U, Th and Zr Most preferably, the metal containing compound will contain a metal selected from the group consisting of Ti, Hf and Zr.

The chiral organometallic complexes of the present invention can be produced by any method. A suitable method for producing the organometallic complexes of the present invention comprises contacting a chiral substituted cyclopentadienyl ligand of general formula III with a metal containing compound as described above, under suitable reaction conditions so as to form the desired chiral organometallic complex, which is typically of general formula V:

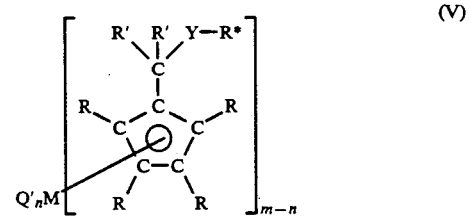

wherein R, R', R*, and Y are as defined above, each Q' may independently be any univalent anionic ligand such as a halide, hydride, or substituted or unsubstituted C1-C20 hydrocarbyl, alkoxide, aryloxide, amide, arylamide, phosphide or arylphosphide, or two ore more Q' together may be an alkylidene or a cyclometallated hydrocarbyl or any other divalent anionic chelating ligand, M is a transition metal as described above, m is the valence or oxidation state of the metal and n is in the range of about 1 to about m-1. Preferably, Q' is a halide selected from the group consisting of chlorine, bromine and iodine.

Generally the enantiomeric excess of the enhanced chiral organometallic complex of the present invention may be any desired enantiomeric excess of either the R or S enantiomer, ranging from just over the racemic mixture to even including essentially all of one enantiomer, and would depend on the desired end use of any catalyst produced from such organometallic complexes. Such desired enantiomeric excess is generally at least about 1 percent. Preferably such enantiomeric excess is at least about 5 percent, and most preferably at least about 50 percent.

Since the reaction of the chiral substituted cyclopentadienyl ligand of general formula III with the metal containing compound, to form the chiral organometallic complex, does not involve the breaking of a bond to the chiral center, the reaction will proceed with a retention of the configuration about that chiral center. This means that the configuration about the chiral center and the enantionmeric excess of the resulting chiral organometallic complex product will be essentially the same as the configuration about the chiral center and the enantiomeric excess of the chiral substituted cyclopentadienyl ligand from which it was derived. Therefore to obtain a chiral substituted organometallic complex product of a desired configuration and enantiomeric excess or purity, the configuration and enantiomeric excess or purity of the reactant chiral substituted cyclopentadienyl ligand will need to be substantially the same as the desired configuration and enantiomeric excess or purity.

The chiral substituted cyclopentadienyl ligand of general formula III and the metal containing compound are generally contacted at a temperature that is sufficient to form the chiral organometallic complex. Such temperature is generally in the range of about −78 to about 200° C. Preferably the temperature is in the range of about −78 to about 100° C. Most preferably the temperature is in the range of from about −78 to about 65° C.

Ligands of general formula III and the metal containing compound generally contacted together at a pressure that is suitable for the formation of the chiral organometallic complex. Suitable pressures include those in the range of about just above 0 psia to about 2000 psig. Preferably the pressures are in the range of from about 1 psia to about 50 psig. Most preferably the pressures are in the range of from about 0 to about 16 psig.

Chiral substituted cyclopentadienyl ligands of general formula III may be contacted together with the metal containing compounds in the presence of any suitable solvent that will facilitate the production of compounds of general formula V. Generally the solvent is selected from the group consisting of ethers, glymes hydrocarbons, and aromatic hydrocarbons. Suitable solvents include ethers such as dimethylether, diethylether and methyethylether, glymes such as monoglyme, ethyl glyme, diglyme, ethyl diglyme, triglyme, butyl diglyme and tetraglyme, THF, DME, Hexane, toluene, and methylene chloride.

The chiral substituted cyclopentadienyl ligands of general formula III and the metal containing compounds are generally contacted together for a time sufficient to form the desired chiral organometallic complexes. Suitable contacting times include those in the range of from about 0.1 minutes to about 24 hours. Preferably, the contacting time is in the range of about 0.5 hours to about 16 hours. Most preferably the contacting time is in the range of 1 to about 8 hours.

The chiral substituted cyclopentadienyl ligands of general formula III and the metal containing compounds are generally contacted together in mole ratios that are suitable for the formation of compounds of desired organometallic complex. Suitable mole ratios of the chiral substituted cyclopentadienyl ligands of general formula III to the metal containing compounds include those in the range of from about 10 to 1 to about 1 to 10. Preferably, the mole ratios are in the range of from about 3 to 1 to about 1 to 3. Most preferably the mole ratios are in the range of about 1 to about 1 to 1.1.

The chiral substituted cyclopentadienyl ligands of general formula III, IIIb and IIIc are suitable as precursors for making chiral substituted organometallic complexes, which can be utilized as components in catalyst systems that are useful in the polymerization hydrogenation, hydroformalation and epoxidation, especially in catalyst systems that are useful in the polymerization of polyolefins. In particular, the chiral catalyst complexes of enhanced enantiomeric purity are useful in controlling particular properties of polyolefins, including melting point and crystallinity.

The chiral organometallic complexes of the present invention are useful as the metallocene component of a supported metallocene alumoxane catalyst for use in gas phase polymerization of olefins. Supported metallocene-alumoxane catalysts and methods for making them are well known. Supported metallocene-alumoxane catalysts for olefin polymerization are described in U.S. Pat. No. 4,701,432 of Welborn. These supported metallocene-alumoxane catalysts are generally obtained by reacting a metallocene and an alumoxane in the presence of the solid support material. The supported catalyst may then be employed either as the sole catalyst component or may be employed in combination with an organometallic cocatalyst.

EXAMPLE

Addition of (R)-(+)-aloha-methylbenzylamine to 1,2,3,4-tetramethylfulyene

To a solution of 1.9 mL of (R)-(+)-alpha-methylbenzylamine (47 mmol) in 30 mL of ether was added 9.3 mL of n-Butyllithium (1.6 M in hexane 14.9mmol) at 0° C. This solution was then allowed to stir at room temperature for 2 hours. Freshly prepared 1,2,3,4-tetramethyl fulvene, 2.0g (14.9 mmol) was added and the reaction mixture refluxed for 8 hours. The reaction mixture was then cooled to room temperature and 1.4 g, 44% yield of (R)-Li[C₅Me₄CH₂NHCH(CH₃)Ph] was isolated by filtration.

The invention has been described with reference to its preferred embodiments. Those of ordinary skill in the art may, upon reading this disclosure, appreciate changes or modifications which do not depart from the scope and spirit or the invention as described above or claimed hereafter.

What is claimed:

1. A method of making enantiomerically enhanced chiral substituted cyclopentadienyl ligands of general formula III:

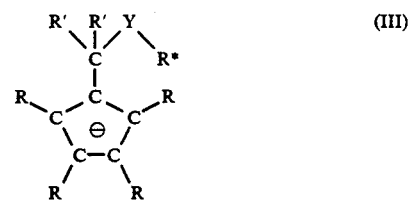

comprising contacting a substituted fulvene compound of general formula I:

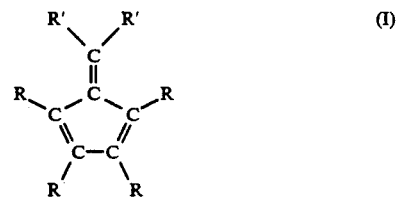

with a enantiomerically enhanced chiral nucleophile, capable of forming ions of general formula II:

R*Y⁻ wherein each R and each R' is independently selected from the group consisting of H, radicals of substituted aliphatic hydrocarbons, unsubstituted aliphatic hydrocarbons, substituted cyclic hydrocarbons, unsubstituted cyclic hydrocarbons, substituted heterocyclic hydrocarbons, and unsubstituted heterocyclic hydrocarbons and two neighboring R groups can be joined together to form a ring of five or more carbon atoms; R* contains at least one chiral carbon center and is selected from the group consisting of enantiomerically enhanced chiral radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons; Y is selected from the group consisting of NR", NH, O, S, C(R")₂, PR" and Si(R")₂; and each R" is independently selected from the group consisting of H radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons.

2. The method of claim 1 wherein the cyclopentadienyl ligand and the nucleophile are contacted together at a temperature in the range of about −78 to about 200° C., at a pressure in the range of about just above 0 psia to about 2000 psig, for a contacting time in the range of about 0.1 minutes to about 24 hours, and at a mole ratio of the ligand to nucleophile in the range of about 10:1 to about 1:10.

3. The method of claim 2 wherein the chiral substituted cyclopentadienyl ligands of general formula III are produced at an enantiomeric excess of at least 1 percent.

4. The method of claim 1 wherein each R is independently selected from the group consisting of radicals of alkyls and aromatics or two R groups are joined together to form a ring of 5 or more carbon atoms; each R' is independently selected from the group consisting of H, and alkyl and aromatic hydrocarbons; R* contains at least one chiral carbon center and is selected from the group consisting of radicals of amino acids, and alkyl and aromatic hydrocarbons; and Y is selected from the group consisting of NH and NR"; and each R" is independently selected from the group consisting of alkyl and aromatic hydrocarbon radicals.

5. The method of claim 4 wherein the cyclopentadienyl ligand and the nucleophile are contacted together at a temperature in the range of about −78 to about 200° C., at a pressure in the range of about just above 0 psia to about 2000 psig, for a contacting time in the range of about 0.1 minutes to about 24 hours, and at a mole ratio of the ligand to nucleophile in the range of about 10:1 to about 1:10.

6. The method of claim 5 wherein the chiral substituted cyclopentadienyl ligands of general formula III are produced at an enantiomeric excess of at least 5 percent.

7. The method of claim 1 wherein the substituted fulvene compound is selected from the group consisting of 1,2,3,4-tetramethylfulvene, 1,2,3,4-tetraethylfulvene and 1,2,3,4,6-pentamethylfulvene, and the chiral nucleophile is an alpha-alkylarylamine selected from the group consisting of alpha-methylbenzyl amine, alpha-ethylbenzyl amine, alpha-propylbenzyl amine, alpha-butylbenzyl amine, alpha-methylnaphtha amine, alpha-ethylnaptha amine, alpha-propylnaptha amine, and alpha-butylnaptha amine.

8. The method of claim 7 wherein the cyclopentadienyl ligand and the nucleophile are contacted together at a temperature in the range of about −50 to about 100° C., at a pressure in the range of about 1 psia to about 50 psig, for a contacting time in the range of about 0.5 hours to about 16 hours, and at a mole ratio of the ligand to nucleophile in the range of about 3:1 to about 1:3.

9. The method of claim 1 wherein the substituted fulvene compound is 1,2,3,4-tetramethylfulvene and the chiral nucleophile is alpha-methylbenzyl amine.

10. The method of claim 9 wherein the cyclopentadienyl ligand and the nucleophile are contacted together at a temperature in the range of about −50 to about 100° C., at a pressure in the range of about 1 psia to about 50 psig, for a contacting time in the range of about 0.5 hours to about 16 hours, and at a mole ratio of the ligand to nucleophile in the range of about 3:1 to about 1:3.

11. The method of claim 10 wherein the chiral substituted cyclopentadienyl ligands of general formula III are produced at an enantiomeric excess of at least 5 percent.

12. The method of claim 10 wherein the cyclopentadienyl ligand and the nucleophile are contacted together at a temperature in the range of about −20 to about 65° C., at a pressure in the range of about 0 psig to about 16 psig, for a contacting time in the range of about 1 to about 8 hours, and at a mole ratio of the ligand to nucleophile in the range of about 1:1:1 to about 1:1.1.

13. An enantiomerically enhanced composition comprising chiral substituted cyclopentadienyl ligands of general formula III:

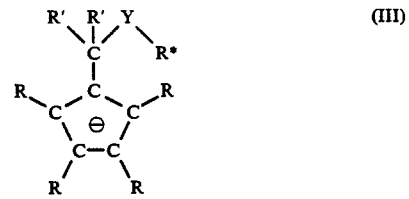

(III)

wherein each R and each R' is independently selected from the group consisting of H, radicals of substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons and two neighboring R groups can be joined together to form a ring of five or more carbon atoms; R* contains at least one chiral carbon center and is selected from the group consisting of enantiomerically enhanced chiral radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons; Y is selected from the group consisting of NR", NH, O, S, C(R")₂, PR" and Si(R")₂; and each R" is independently selected from the group consisting of H, radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons.

14. The composition of claim 13 wherein each R is independently selected from the group consisting of radicals of alkyls and aromatics or two R groups are joined together to form a ring of 5 or more carbon atoms; each R' is independently selected from the group consisting of H, and radicals of alkyl and aromatic hydrocarbons; R* contains at least on chiral carbon center and is selected from the group consisting of radicals of amino acids, and alkyl and aromatic hydrocarbons; and Y is selected from the group consisting of NH and NR"; and each R" is independently selected from the group consisting of alkyl and aromatic hydrocarbon radicals.

15. The composition of claim 14 wherein each R is independently selected from the group consisting of methyl, ethyl, propyl; R' is H; and —Y—R* is an alpha-alkylarylamine radical selected from the group consisting of radicals of alpha-methylbenzyl amine, alpha-ethylbenzyl amine, alpha-propylbenzyl amine, alpha-butylbenzyl amine, alpha-methylnaphtha amine, alpha-ethylnaptha amine, alpha-propylnaptha amine, and alpha-butylnaptha amine.

16. The composition of claim 15 wherein each R is independently selected from the group consisting of methyl, ethyl and propyl; R' is H; and —Y—R* is an alpha-methylbenzyl amine radical.

17. An enantiomerically enhanced composition comprising chiral substituted cyclopentadiene compounds of general formula IIIb:

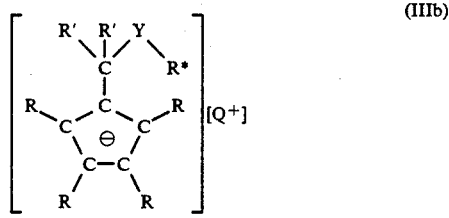

wherein each R and each R' is independently selected from the group consisting of H, radicals of substituted aliphatic hydrocarbons, unsubstituted aliphatic hydrocarbons, substituted cyclic hydrocarbons, unsubstituted cyclic hydrocarbons, substituted heterocyclic hydrocarbons, unsubstituted heterocyclic hydrocarbons and two neighboring R groups can be joined together to form a ring of five or more carbon atoms R* contains at least one chiral carbon center and is selected from the group consisting of enantiomerically enhanced chiral radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons; Y is selected from the group consisting of NR", NH, O, S, C(R")2, PR" and Si(R")2; each R" is independently selected from the group consisting of H, radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons, and Q is selected from the group consisting of thallium, potassium, lithium, sodium and MgX, wherein X is selected from the group consisting of Br, Cl and I.

18. The composition of claim 17 wherein each R is independently selected from the group consisting of radicals of alkyls and aromatics or two R groups are joined together to form a ring of 5 or more carbon atoms; each R' is independently selected from the group consisting of H, and radicals of alkyl and aromatic hydrocarbons; R* contains at least on chiral carbon center and is selected from the group consisting of radicals of amino acids, and alkyl and aromatic hydrocarbons; and Y is selected from the group consisting of NH and NR"; and each R" is independently selected from the group consisting of alkyl and aromatic hydrocarbon radicals.

19. The composition of claim 18 wherein the enantiomeric enhancement is an enantiomeric excess of at least 5 percent.

20. The composition of claim 18 wherein each R is independently selected from the group consisting of methyl, ethyl, propyl or two R groups are joined together to form a 6 numbered ring; R' is H; and —Y—R* is an alpha-alkylarylamine radical selected from the group consisting of radicals of alpha-methylbenzyl amine, alpha-ethylbenzyl amine, alpha-propylbenzyl amine, alpha-butylbenzyl amine, alpha-methylnaphtha amine, alpha-ethylnaptha amine, alpha-propylnaptha amine, and alpha-butylnaptha amine.

21. The composition of claim 20 wherein each R is independently selected from the group consisting of methyl, ethyl and propyl or two R groups are joined together to form a 6 numbered ring; R' is H; and -Y-R* is an alpha-methylbenzyl amine radical.

22. The composition of claim 21 wherein the enantiomeric enhancement is an enantiomeric excess of at least 5 percent.

23. An enantiomerically enhanced composition comprising chiral compounds of general formula V:

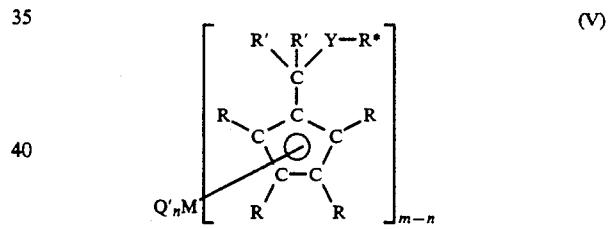

wherein each R and each R' is independently selected from the group consisting of H, radicals of substituted aliphatic hydrocarbons, unsubstituted aliphatic hydrocarbons, substituted cyclic hydrocarbons, unsubstituted cyclic hydrocarbons, substituted heterocyclic hydrocarbons, unsubstituted heterocyclic hydrocarbons and two neighboring R groups can be joined together to form a ring of five or more carbon atoms; R* contains at least one chiral carbon center and is selected from the group consisting of enantiomerically enhanced chiral radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons; Y is selected from the group consisting of NR", NH, O, S, C(R")2, PR" and Si(R")2; each R" is independently selected from the group consisting of H, radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons; each Q' is independently a univalent anionic ligand selected from the group consisting of a halide, hydride, substituted or unsubstituted C₁-C₂₀ hydrocarbyl, alkoxide, aryloxide, amide, arylamide, phosphide and arylphosphide; M is a transition metal selected from the group consisting of Group IIIB-VIIIB transition metals; m is the transition state of the metal; and n is in the range of about 1 to about m−1.

24. The composition of claim 23 wherein each R is independently selected from the group consisting of radicals of alkyls and aromatics or two R groups are joined together to form a ring of 5 or more carbon atoms; each R' is independently selected from the group consisting of H, and radicals of alkyl and aromatic hydrocarbons; R* contains at least on chiral carbon center and is selected from the group consisting of radicals of amino acids, and alkyl and aromatic hydrocarbons; and Y is selected from the group consisting of NH and NR''; and each R'' is independently selected from the group consisting of alkyl and aromatic hydrocarbon radicals; each Q' is a halogen independently selected from the group consisting of chlorine, bromine and iodine; and M is a transition metal selected from the group consisting of Group IV B, Group VI B and Group VIII B transition metals.

25. The composition of claim 24 wherein each R is independently selected from the group consisting of methyl, ethyl, propyl or two R groups are joined together to form a 6 numbered ring; R' is H; and —Y—R* is an alpha-alkylarylamine radical selected from the group consisting of radicals of alpha-methylbenzyl amine, alpha-ethylbenzyl amine, alpha-propylbenzyl amine, alpha-butylbenzyl amine, alpha-methylnaphtha amine, alpha-ethylnaptha amine, alpha-propylnaptha amine, and alpha-butylnaptha amine.

26. The composition of claim 25 wherein the enantiomeric enhancement is an enantiomeric excess of at least 5 percent.

27. The composition of claim 26 wherein M is a Group IV metal.

28. The composition of claim 27 wherein —Y—R* is an alpha-methylbenyzlamine radical.

29. The composition of claim 28 wherein each R is methyl.

30. The composition of claim 25 wherein M is selected from titanium, hafnium and zirconium.

31. An enantiomerically enhanced composition comprising chiral substituted cyclopentadiene compounds of general formula IIIc:

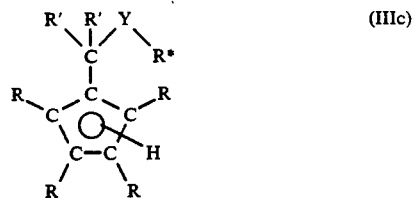

(IIIc)

wherein each R and each R' is independently selected from the group consisting of H, radicals of substituted aliphatic hydrocarbons, unsubstituted aliphatic hydrocarbons, substituted cyclic hydrocarbons, unsubstituted cyclic hydrocarbons, substituted heterocyclic hydrocarbons, unsubstituted heterocyclic hydrocarbons and two neighboring R groups can be joined together to form a ring of five or more carbon atoms; R* contains at least one chiral carbon center and is selected from the group consisting of enantiomerically enhanced chiral radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons; Y is selected from the group consisting of NR'', NH, O, S, C(R'')₂, PR'' and Si(R'')₂; each R'' is independently selected from the group consisting of H, radicals of amino acids, substituted aliphatic hydrocarbons, unsubstituted aliphatic hydrocarbons, substituted cyclic hydrocarbons, unsubstituted cyclic hydrocarbons, substituted heterocyclic hydrocarbons and unsubstituted heterocyclic hydrocarbons.

32. The composition of claim 31 wherein each R is independently selected from the group consisting of radicals of alkyls and aromatics or two R groups are joined together to form a ring of 5 or more carbon atoms; each R' is independently selected from the group consisting of H, and radicals of alkyl and aromatic hydrocarbons; R* contains at least on chiral carbon center and is selected from the group consisting of radicals of amino acids, and alkyl and aromatic hydrocarbons; and Y is selected from the group consisting of NH and NR''; and each R'' is independently selected from the group consisting of alkyl and aromatic hydrocarbon radicals.

33. The composition of claim 32 wherein the enantiomeric enhancement is an enantiomeric excess of at least 5 percent.

34. The composition of claim 33 wherein each R is independently selected from the group consisting of methyl, ethyl, propyl or two R groups are joined together to form a 6 numbered ring; R' is H; and —Y—R'' is an alpha-alkylarylamine radical selected from the group consisting of radicals of alpha-methylbenzyl amine, alpha-ethylbenzyl amine, alpha-propylbenzyl amine, alpha-butylbenzyl amine, alpha-methylnaphtha amine, alpha-ethylnaptha amine, alpha-propylnaptha amine, and alpha-butylnaptha amine.

35. The cOmposition of claim 34 wherein each R is independently selected from the group consisting of methyl, ethyl and propyl or two R groups are joined together to form a 6 numbered ring; R' is H; and —Y—R'' is an alpha-methylbenzyl amine radical.

* * * * *